United States Patent [19]
Sirinyan et al.

[11] Patent Number: 5,846,997
[45] Date of Patent: Dec. 8, 1998

[54] LIQUID FORMULATIONS

[75] Inventors: Kirkor Sirinyan, Bergisch Gladbach; Rainer Sonneck, Leverkusen; Klaus Mrusek, Bergisch Gladbach, all of Germany

[73] Assignee: Bayer Aktiengesellschaft, Leverkusen, Germany

[21] Appl. No.: 639,597

[22] Filed: Apr. 29, 1996

[30] Foreign Application Priority Data

May 5, 1995 [DE] Germany .......................... 195 16 522.5

[51] Int. Cl.⁶ .......................... A01N 47/22; A01N 47/10; A01N 25/02
[52] U.S. Cl. .......................... 514/490; 514/476; 514/478; 514/937; 514/938; 514/970
[58] Field of Search ..................................... 514/476, 467, 514/478, 479, 480, 481, 489, 490, 937, 970

[56] References Cited

U.S. PATENT DOCUMENTS

| | | | |
|---|---|---|---|
| 4,452,630 | 6/1984 | Dal Moro et al. ...................... | 504/301 |
| 4,452,632 | 6/1984 | Nickey et al. .......................... | 504/123 |
| 5,160,528 | 11/1992 | Chaudhuri et al. ..................... | 514/788 |

FOREIGN PATENT DOCUMENTS

| | | |
|---|---|---|
| 1152429 | 8/1983 | Canada . |
| 0 648414 A2 | 4/1995 | European Pat. Off. . |
| 30 27 767 A1 | 2/1981 | Germany . |
| 41 40 928 A1 | 6/1993 | Germany . |

*Primary Examiner*—John Pak
*Attorney, Agent, or Firm*—Sprung Kramer Schaefer & Briscoe

[57] ABSTRACT

The present invention relates to water-emulsifiable liquid formulations of insecticidal active compounds, characterized in that they contain a) 2.5 to 30% of active compound, b) 5 to 77.5% of a mixture of benzyl acetate and an alcohol in the ratio 25–95% to 5–75%, c) 2.5 to 20% of formulation auxiliary.

5 Claims, No Drawings

LIQUID FORMULATIONS

The present invention relates to liquid formulations of insecticidal active compounds, which are emulsifiable in water.

When using insecticidal active compounds, which in some cases are poorly water-soluble, in the form of water-diluted spray compositions, it is necessary to prepare formulations of these active compounds which are emulsifiable with water. To do this, the active compounds are usually dissolved in organic solvents and mixed with emulsifiers and, if appropriate, other additives. The preparation of such formulations is described, for example, in DE-OS (German Published Specification) 3 027 767. The solvents used here are, inter alia, dimethyl-formamide and dimethyl acetate. It is desirable to replace these solvents by those which are readily tolerable and toxicologically acceptable.

The present invention relates to
1. Water-emulsifiable liquid formulations of insecticidal active compounds, characterized in that they contain
    a) 2.5 to 30% of active compound,
    b) 5 to 77.5% of a mixture of benzyl acetate and an alcohol in the ratio 25–95% to 5–75%,
    c) 2.5 to 20% of formulation auxiliary.
    (The % data are percent by weight.)

The formulations according to the invention are outstandingly suitable for the preparation of spray mixtures for professional use in pest control in the household, industry, stables etc. They are distinguished by outstanding storage stability and very good emulsifiability in water. They are additionally cost-effective to prepare the solvents selected are unproblematical for the user.

Active compounds which may preferably be are the insecticides employed in the hygiene and professional pest control sector, such as carbamates, pyrethroids, phosphoric acid esters, and also mixtures of these active compounds with synergists.

Carbamates which may be mentioned are substituted phenyl- and naphthyl-carbamates.

The following may preferably be mentioned:
2-isobutylphenyl N-methylcarbamate,
4-dimethylamino-3-methyl-phenyl N-methylcarbamate,
2-isopropoxy-phenyl N-methylcarbamate,
1-naphthyl N-methylcarbamate,
m-tolyl N-methylcarbamate,
3,4-xylyl N-methylcarbamate,
3,5-xylyl N-methylcarbamate,
2-[1,3-dioxolan-2-yl]-phenyl N-methylcarbamate.

Pyrethroids which may preferably be mentioned are the compounds having the common names permethrin, cypermethrin, deltamethrin, cyfluthrin.

Phosphoric acid esters which may preferably be mentioned are the compounds having the common names fenitrothion, dichlorvos, trichlorfon.

A synergist for these compounds which may preferably be mentioned is piperonyl butoxide.

The active compounds are present to 2.5 to 30% by weight, preferably 5 to 25%, very preferably 15 to 20%.

The solvent according to the invention employed is a mixture of benzyl acetate and an alcohol. Alcohols which may preferably be mentioned are aliphatic $C_{1-8}$-alcohols which are optionally substituted, and further benzyl alcohol or tetrahydrofurfuryl alcohol.

Particularly preferably, mention may be made of ethanol, isopropanol, n-butanol, and benzyl alcohol.

In the formulation according to the invention, the solvent mass lies to 5 to 77.5% by weight, preferably 25 to 75%, very particularly preferably 50–75%.

In the formulation according to the invention, benzyl acetate is present to 25 to 95% by weight, preferably 20 to 75%, particularly preferably 25 to 50%.

The alcohols (based on the total solvent mass) are present to 5 to 75% by weight, preferably 50 to 75%, particularly preferably 30 to 50%.

The formulations according to the invention can additionally contain customary auxiliaries such as emulsifiers, stabilizers, antioxidants or odour-marking agents.

Emulsifiers which may be mentioned are: non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-Na-N-lauryl-β-iminodipropionate or lecithin;

anionic surfactants, such as Na laurylsulphate, fatty alcohol ether sulphates, mono/dialkylpolyglycol ether orthophosphoric acid ester monoethanolamine salt; cationic surfactants such as cetyltrimethylammonium chloride.

Stabilizers and antioxidants which may be mentioned are sulphites or meta-bisulphites such as potassium metabisulphite; organic acids such as citric acid; ascorbic acid; phenols, butylhydroxytoluene, butylhydroxyanisole, tocopherol.

Emulsifiers are contained in the formulations according to the invention to 2.5 to 17.5% by weight, particularly preferably 5 to 15%.

Stabilizers and antioxidants are preferably contained to 0.1 to 0.5% by weight, particularly preferably to 0.1 to 0.25%.

Odour-marking agents are, for example, mixtures of organic fatty acid esters. They are preferably contained in the formulations according to the invention to 0.1 to 2% by weight.

The following examples are intended to illustrate the invention:

EXAMPLE 1

Propoxur [Cas. No. 114-26-1] 20 g
Emulsifier PS 16(1) 12 g
Emulsifier 1371 A$^{(2)}$ 2 g
Tetrahydrofurfuryl alcohol 7.5 g
Benzyl acetate 61.78 g (to 100 ml)
Citric acid 0.1 g
BHT (butylhydroxytoluene) 0.1 g $^{(1)}$Emulsifier PS 16 is an alkylaryl polyglycol ether of Bayer AG.
$^{(2)}$Emulsifier 1371 A is an alkylarylsulphonate (67% strength in n-butanol of Bayer AG.

EXAMPLE 2

Propoxur 11 g
Benzyl acetate 60%, benzyl alcohol 40% 77.9 g (to 100 ml)
Emulsifier 1371 A 5 g
Emulsogen EL$^{(3)}$ 8 g
Citric acid 0.1 g
BHT 0.1 g $^{(3)}$Emulsogen EL is an ethoxylated vegetable oil of Hoechst AG.

EXAMPLE 3

Propoxur 20 g
Emulsogen EL$^{(3)}$ 8 g
Emulsifier 1371 A 5 g
Citric acid 0.1 g
BHT 0.1 g Malodur Counteract[(4)] 2.0 g Benzyl acetate 35%, benzyl alcohol 65% 69.1 g (to 100 ml)

[(4)] Malodur Conteract is a fatty acid-based odour-masking agent of Haarmann and Reimer.

Testing for biological residual action

Experimental method

To determine the action of the formulation indicated in Example 3, spray mixtures were prepared. Using these spray mixtures various substrates PVC floor covering, varnished plywood, glazed or unglazed tiles were sprayed at specific application rates (mg of a.i./m$^2$).

A week after treatment up to 4 weeks weekly, then further after 6, 8 and 12 weeks five cockroaches were placed on the respective substrates. The animals were kept on the treated surfaces by means of a soapstoned glass ring (diameters; 9.5 cm; 5.5 cm) and remained there for 24 hours.

Assessment for percentage destruction was carried out after 15 and 30 minutes, calculated from the time of addition, and also hourly after 1 to 6 hours. Further assessments were carried out after 8 and 24 hours (cf. Tab. 1)

As can be seen from Tab. 1, the spray mixtures based on the liquid formulations according to the invention have an outstanding biological action on various.

The storage stability of the liquid formulations or spray mixtures thereof indicated in Examples 1–3 is outstanding.

a) 2.5 to 30% by weight of the liquid-formulation of 2-isopropoxy-phenyl-N-methylcarbamate;

b) 5 to 77.5% by weight of the liquid-formulation of a solvent mixture consisting of benzyl acetate and benzyl alcohol, wherein benzyl acetate represents 25 to 50% by weight of said solvent mixture and benzyl alcohol represents 50 to 75% by weight of said solvent mixture; and c) 2.5 to 20% by weight of the liquid-formulation of a formulation auxiliary.

2. A water-emulsifiable liquid-formulation according to claim 1, wherein the formulation auxiliay comprises stabilizers or antioxidants in an amount of from 0.1 to 0.5% by weight of the liquid-formulation.

3. A water-emulsifiable liquid formulation according to claim 2, wherein the stabilizers are based on organic acids.

4. A water-emulsifiable liquid formulation according to claim 2, wherein the antioxidants are based on phenols.

5. A method of combating insects comprising administering to the insects or their habitat or to an area from which it is desired to exclude said insects an effective amount therefor of a water-emulsifiable liquid-formulation according to claim 1.

TABLE 1

Residual actionon various substrates

| Animal species | Application rate mg of a.i./m$^2$ | Substrate | Age of the treatment in weeks | 100% mortality after hours within an exposure time of twenty four hours |
|---|---|---|---|---|
| Blattella germanica L 5 | 500 | PVC | 2 | 24 h = 80% |
| | 1000 | " | 6 | 4 h |
| | 500 | varnished wood | 6 | 24 h = 80% |
| | 100 | " | 12 | 24 h = 80% |
| | 500 | glazed tile | 12 | 8 h |
| | 100 | " | 12 | 1 h |
| | 500 | unglazed tile | 8 | 2 h |
| | 100 | | 12 | 2 h |
| Blatta orientalis L 5 | 500 | PVC | 12 | 24 h |
| | 1000 | " | 12 | 3 h |
| | 500 | varnished wood | 12 | 3 h |
| | 1000 | " | 12 | 4 h |
| | 500 | glazed tile | 12 | 4 h |
| | 1000 | " | 12 | 1 h |
| | 500 | unglazed tile | 8 | 5 h |
| | 1000 | " | 12 | 3 h |

We claim:

1. A water-emulsifiable liquid-formulation comprising:

* * * * *